US005500139A

United States Patent [19]

Rahman et al.

[11] Patent Number: 5,500,139

[45] Date of Patent: Mar. 19, 1996

[54] BIODEGRADABLE FABRIC CONDITIONING MOLECULES BASED ON GLYCERIC ACID

[75] Inventors: Mohammad A. Rahman, River Edge; Robert W. R. Humphreys, Annandale; Shang-Ren Wu, Mahwah, all of N.J.

[73] Assignee: Lever Brothers Company, Division of Conopco, Inc., New York, N.Y.

[21] Appl. No.: 391,795

[22] Filed: Feb. 21, 1995

Related U.S. Application Data

[63] Continuation-in-part of Ser. No. 260,641, Jun. 16, 1994, abandoned.

[51] Int. Cl.$^6$ .......................... D06M 13/46; C07C 69/52

[52] U.S. Cl. .......................... 252/8.8; 252/8.6; 252/8.7; 252/8.75; 560/196; 564/199

[58] Field of Search .......................... 560/196; 564/199; 252/8.6, 8.7, 8.75, 8.8

[56] References Cited

U.S. PATENT DOCUMENTS

| | | | |
|---|---|---|---|
| 4,137,180 | 1/1979 | Naik et al. | 252/8.8 |
| 4,767,547 | 8/1988 | Straathof et al. | 252/8.8 |
| 4,789,491 | 12/1988 | Chang et al. | 252/8.75 |
| 4,913,828 | 4/1990 | Caswell et al. | 252/8.8 |
| 5,254,269 | 10/1993 | Taylor et al. | 252/8.6 |

OTHER PUBLICATIONS

Chemical Abstracts Registry File, Registry #122147–94–8, "Mucamide, N,N'–dibenzyl–N,N'–bis (2–diethylaminoethyl)–, tetraacetate". [No date].

Chemical Abstracts Registry File, Registry #121291–43–8, "Mucamide, N,N'–dibenzyl–N,N'–bis (2–diethylaminoethyl)–, tetraacetate, dihydrochloride". [No date].

Chemical Abstracts Registry File, Registry #109129–14 8, "Mucoylbis [(benzylimino) ethylene]bis[diethylmethylammonium iodide tetraacetate". [No date].

*Primary Examiner*—Anthony Green
*Attorney, Agent, or Firm*—A. Kate Huffman

[57] ABSTRACT

Novel fabric conditioning agents which contain either an ester or a NH link between a glyceric carboxyl group and a quaternary ammonium group are described. The compounds based on glyceric acid are both effective fabric conditioners and biodegradable, and may be formulated in any conventional physical form to form a fabric conditioning composition. A method of using the composition is also described.

14 Claims, No Drawings

BIODEGRADABLE FABRIC CONDITIONING MOLECULES BASED ON GLYCERIC ACID

RELATED APPLICATIONS

This application is a continuation-in-part of U.S. Ser. No. 08/260,641 filed Jun. 16, 1994.

FIELD OF THE INVENTION

This invention pertains to novel compounds which are both effective fabric conditioners and biodegradable.

BACKGROUND OF THE INVENTION

Quaternary ammonium salts such as 1,2-ditallowyl oxy-3-trimethyl ammoniopropane chloride are known as effective fabric conditioning agents which are also biodegradable as described in U.S. Pat. Nos. 4,137,180; 4,767,547 and 4,789,491. The biodegradable cationic diester compounds described in column 1 of 4,137,180 are preferred fabric conditioning molecules.

However, it has been observed that these fabric conditioning molecules degrade by hydrolization of one of the ester moieties from the molecule resulting in a monoester form of the molecules which at certain levels may cause aquatic toxicity.

Therefore, there is a need for novel molecules which are both effective fabric conditioners and which are biodegradable.

SUMMARY OF THE INVENTION

It is thus an objective of the invention to provide novel compounds which are both effective fabric conditioners and which are biodegradable.

Another objective of the invention is to provide fabric conditioning compositions which are useful for fabric softening and static control in a variety of stable physical forms.

A further object of the invention is to provide environmentally friendly fabric conditioning compositions which are good fabric softeners.

Yet another object of the invention is to provide a process for laundering fabrics which yields effective fabric conditioning using the novel cationic molecules of the invention.

DETAILED DESCRIPTION OF PREFERRED EMBODIMENTS

This invention relates to novel compounds of formula

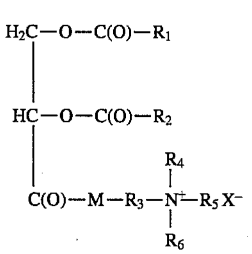

I wherein $R_1$ and $R_2$ are each independently a $C_{15}$ to $C_{28}$ branched or straight chain alkyl, alkenyl or hydroxyalkyl, $R_3$ is $C_{1-6}$ straight or branched alkyl, alkenyl or aryl, $R_4$, $R_5$ and $R_6$ are each independently a $C_1$–$C_6$ straight or branched alkyl, alkenyl, aryl, or H provided that at least two of $R_4$, $R_5$ and $R_6$ are not H, M is O, NH or $NR_7$, $R_7$ is a $C_{1-6}$ alkyl or alkenyl which is unsubstituted or hydroxy substituted and X is an anion which is water soluble. The $R_1$, $R_2$, $R_3$, $R_4$, $R_5$, $R_6$ and $R_7$ moieties are preferably straight chains.

The anion $X^-$ and the molecule is preferably the anion of a strong acid such as a halide, sulfate, particularly methyl sulfate, or nitrate. X is preferably chloride, bromide, iodide, sulfate (especially preferred methyl sulfate. The anion may carry a double charge in which case $X^-$ represents half a group.

Preferred compounds of formula I are those in which $R_1$ and $R_2$ are each independently a $C_{15}$ to $C_{28}$ straight or branched chain alkyl, $R_3$ is a $C_{1-6}$ straight chain alkyl, $R_4$, $R_5$ and $R_6$ are each independently a $C_{1-6}$ straight chain alkyl and M is O, NH or $NR_7$ wherein $R_7$ is an unsubstituted $C_{1-6}$ alkyl. Most preferred compounds of formula I are those in which $R_1$ and $R_2$ are each independently a $C_{15}$ to $C_{20}$ straight or branched chain alkyl, $R_3$, $R_4$, $R_5$ and $R_6$ are each independently a $C_{1-3}$ straight chain alkyl and M is O or NH.

Examples of compounds of formula I include trimethylammonium ethyl 2,3-dipalmitoyl glycerate chloride; trimethylammonium ethyl 2,3 distearoyl glycerate chloride; and trimethylammonium ethyl 2,3-dipalmitoyl glyceramide chloride.

Preparation

When the compounds of formula I are those wherein M is an oxygen atom, the compounds are prepared as follows:

Glyceric acid is converted to methyl glycerate by esterification with a lower alcohol having up to 3 carbons using an acid catalyst (e.g.,$CH_3SO_3^H$, hydrogen chloride). Methyl glycerate is then transesterified with a halide alcohol having up to 6 carbons in the presence of a catalytic amount of an acid to haloalkyl glycerate. The resulting ester is further esterified with a fatty acid chloride in methylene chloride or tetrahydrofuran in the presence of pyridine to give a triester. The ester is then quaternized with trimethylamine in dry tetrahydrofuran to give an ester quat of Formula I.

When the compounds of formula I are those in which M is NH, the compounds are prepared as follows:

Methyl glycerate is heated to a temperature of about 50°–70° C. in a lower alkyl diamine having up to 6 carbons to give an alkyl glyceramide. The amide obtained is esterified with long chain fatty acids to give a glyceramide diester which is then quaternized with an alkyl halide having 1–3 carbons to give compounds of formula 1.

Examples of suitable alkyl diamines are N,N dimethyl ethyl diamine and N,N dimethylpropyl diamine.

Alternatively, compounds of formula I containing the ester link between the glyceric carboxyl group and the quaternary ammonium group may be synthesized by epoxidating a quaternary ammonium acrylate and then esterifying the compound with fatty acids.

Compounds of formula I containing an amide link may alternatively be synthesized by epoxidating a quaternary ammonium acrylamide followed by esterification with a fatty acid.

Fabric Conditioning Compositions

The novel compounds may be formulated in a variety of physical forms to form a fabric conditioning composition. Such a composition would comprise from about 1 to about 99 wt. % of a compound of formula I, and from about 1 to about 99 wt. % water.

Such compositions may be prepared by any conventional method known in the art.

Additional Fabric Conditioning Components

It may be understood that the compounds of the invention may be combined with conventional fabric conditioning components to form a mixture of fabric conditioning actives useful in preparing fabric conditioning compositions. Such conventional conditioning agents include acyclic quaternary ammonium salts such as ditallowdimethylammonium salts, cyclic quaternary ammonium salts, particularly those of the imidazolinium type, diamido quaternary ammonium salts, tertiary fatty amines having at least 1 and preferably 2 $C_8$ to $C_{30}$ alkyl chains, carboxylic acids having 8 to 30 carbon atoms and one carboxylic group per molecule, esters of polyhydric alcohol such as sorbitan esters or glycerolstearate, fatty alcohols, ethoxylated fatty alcohols, ethoxylated fatty amines, mineral oils, polyols such as polyethyleneglycol, silicone oils and mixtures thereof. Suitable conventional fabric conditioning compounds are described in Taylor et al., U.S. Pat. No. 5,254,269, herein incorporated by reference.

Optional Components

Additionally, one or more optional additives may be incorporated in the fabric conditioning composition selected from the group consisting of perfumes, dyes, pigments, opacifiers, germicides, optical brighteners, fluorescers, anti-corrosion agents and preservatives. The amount of each additive in the composition is up to about 0.5% by weight.

Detergent Formulations

It has been found that the conditioning compositions of the present invention can be incorporated into both granular and liquid detergent formulations with little detrimental effect on cleaning.

The compositions are typically used at levels up to about 30% of the detergent composition, preferably from about 5 to 20% of the composition.

Detergent Surfactant

Detergent surfactant included in the detergent formulations of the invention may vary from 1% to about 98% by weight of the composition depending on the particular surfactant(s) used and the cleaning effects desired.

Preferably, the surfactant is present in an amount of from about 10 to 60% by weight of the composition. Combinations of anionic, preferably alkyl sulfates, alkyl ethoxylated sulfates, linear alkyl benzene sulfonates, and nonionic, preferably alkyl polyethoxylated alcohol surfactants are preferred for optimum cleaning, softening and antistatic performance. It may be appreciated that other classes of surfactants such as ampholytic, zwitterionic or cationic surfactants may also be used as known in the art. As generally known, granular detergents incorporate the salt forms of the surfactants while liquid detergents incorporate the acid form where stable. Examples of surfactants within the scope of the invention are described in U.S. Pat. No. 4,913,828 issued to Caswell et al., herein incorporated by reference.

Builders, accumulating agents and soil release agents known in the art may also be used in the detergent formulations. Examples of suitable such components are described in Caswell et al., U.S. Pat. No. 4,913,828, herein incorporated by reference.

Other Optional Detergent Ingredients

Optional ingredients for the detergent compositions of the present invention other than those discussed above include hydrotropes, solubilizing agents, suds suppressers, soil suspending agents, corrosion inhibitors, dyes, fillers, optical brighteners, germicides, pH adjusting agents, enzyme stabilizing agents, bleaches, bleach activators, perfumes and the like.

The following non-limiting examples illustrate the compounds, compositions and method of the present invention. All percentages, parts and ratios used herein are by weight unless otherwise specified.

EXAMPLE 1

Trimethylammonium ethyl 2,3-dipalmitoyl glycerate chloride (GEQ) was prepared as follows:

To a solution of glyceric acid (25 g 0.24 moles) in dry methanol (150 mL) was added hydrogen chloride solution (10 mL, 2% solution in methanol) and refluxed the solution under nitrogen for 10 h. The free acid was neutralized by adding anhydrous sodium carbonate. After filtration, a rotary evaporator was used to remove the solvent yielding 24.8 grams methyl glycerate. The compound showed the following characteristics: $^1$H NMR (200 MHz, $CDCl_3$), δ 3.80 (s, 3H, $CO_2CH_3$), 3.87 (m, 4H, $CH_2$, 2 OH), 4.30 (t, 1H, CH), $^{13}$C NMR (50 MHz,$CDCl_3$), δ 52.27, 63.82, 71.74, 173.16.

A mixture of methyl glycerate (2 g, 0.17 moles) and bromoethanol (5.28 g, 0.42 moles was heated at 60° C. under nitrogen in the presence of a catalytic amount of p-toluene sulfonic acid for 10 h. The excess bromoethanol was removed on rotary evaporator under reduced pressure. The crude mixture was diluted with large volume of chloroform (100 mL) and the free acid was neutralized by adding anhydrous sodium carbonate. Filtration and removal of the solvent gave the crude product which was purified by chromatography on a silica gel column eluting with chloroform:methanol (9:1). Removal of the solvent on a rotary evaporator gave bromoethyl glycerate (3.26 g, 92% yield) which showed the following characteristics: $^1$H NMR (200 MHz, $CDCl_3$), δ 3.52 (m, 2H, $CH_2Br$), 3.90 (m, 2H,$CO_2CH_2$), 4.27 (s, 2H, OH), 4.36 (m, 2H, $CH_2OH$), 4.52 (m, 1 H, CH), $^{13}$C NMR (50 MHz, $CDCl_3$) δ 28.42, 63.76, 64.50, 71.58, 172.13.

To a solution of bromoethyl glycerate (3.0 g, 14.08 mmol) in dry methylene chloride (100 mL) at 0° C. was added pyridine (10 mL) and palmitoyl chloride (9.66 g, 35.70 mmol) followed by a catalytic amount of N,N-dimethylaminopyridine. The reaction mixture was stirred at 0° C. under nitrogen for 3 h and then at room temperature overnight. The reaction mixture was diluted with methylene chloride (200 mL) and washed with dilute hydrochloric acid solution (3×10 mL), water (3×20 mL) and dried over anhydrous sodium sulfate. After filtration, the solvent was removed on a rotary evaporator and the residue was purified on a silica gel column eluting with hexane: ethyl acetate (9:1). Removal of the solvent gave the pure 2,3 dipalmitoyl bromoethyl glycerate (8.93 g, 92% yield). The compound showed the following characteristics: $^1$H NMR (200 MHz, $CDCl_3$), δ 0.87 (t, 6H, $CH_3$), 1.25 (br, $CH_2$), 1.56 (m, $CH_2$), 2.34 (m, 4H, $CH_2$), 3.68 (t, CH), 4.32 (m, $CH_2$), $^{13}$C NMR (50 MHz, $CDCl_3$), δ 13.89, 22.51,24.48, 24.53, 24.63, 25.29, 27.74, 28.85, 28.86, 29.09, 29.20, 29.30, 29.50, 29.52, 31.75, 33.55, 3374, 34.73, 62.04, 64.57, 69.88, 166.69, 172.43, 172.70, MS (CI, isobutane), $MH^+$, 689.8.

2,3-Dipalmitoylbromoethyl glycerate (1.2 g, 0.017 moles) was dissolved in anhydrous tetrahydrofuran (20 mL) and transferred to a pressure reactor. Trimethylamine (10 mL) was condensed using dry ice/acetone condenser and quickly transferred to the reactor and closed. The reactor was placed in an oil bath and heated at 60° C. for 2 h. The reactor was allowed to cool to room temperature and then the excess trimethylamine was removed by flushing nitrogen through the reactor and the liberated gas was allowed to pass through hydrogen chloride solution. The solvent was removed on a rotary evaporator and the solid 2,3-dipalmitoylbromoethyl glycerate was crystallized from methanol:ether. The compound showed the following characteristics: $^1$H NMR (200 MHz, $CDCl_3$), δ 0.88 (t, $CH_3$), 1.28 (br, $CH_2$), 1.62 (m, $CH_2$), 2.22 (m, $CH_2$), 3.52 (s, $CH_3$), 4.21 (m, $CH_2$), 4.62 (m, CH), $^{13}$C NMR (50 MHz, $CDCl_3$) δ 13.71, 22.29, 24.38, 24.47, 25.06, 28.69, 28.97, 29.15, 29.32, 31.53, 33.38, 33.59, 34.54, 53.91,60.09, 62.04, 64.57, 69.88, 166.38, 172.63, 172.97, MS (FAB) $C^+$, 668.6.

An ion exchange resin (10 g, AG. 2-x8 Resin Chloride Form) was washed several times with deionized water in a column until the pH was neutral and then with methanol. A solution of bromide quat (2 g) in small amount of methanol (2 mL) was loaded on the column and eluted with ethyl acetate. This process was repeated until the complete conversion of bromide to chloride ion. The exchange of bromide to chloride was determined by X-ray fluorescence method and trimethyl ammonium ethyl 2,3-dipalmitoyl glycerate chloride was obtained having the following characteristics: m.p. 55°–56° C., $^{1}$H NMR (200 MHz, $CDCl_3$), δ 0.89 (t, 6H, $CH_3$), 1.29 (br, $CH_2$), 1.53 (m, $CH_2$), 2.28 (m, $CH_2$), 3.52 (s, $CH_3$), 4.23 (m, $CH_2$), 4.62 (m, CH), $^{13}$C NMR (50 MHz, $CDCl_3$), δ 13.87, 22.46, 24.60, 24.68, 28.84, 29.14, 29.26, 29.47, 31.70, 33.54, 33.71,3385, 40.88, 54.21,62.05, 64.80, 69.85, 166.83, 172.55, 172.85, MS (FAB), $C^+$, 668.6.

EXAMPLE 2

Trimethylammonium ethyl 2,3-dipalmitoyl glyceramide chloride (GAQ) was prepared as follows:

N,N-Dimethylethyldiamine (2.19 mL, 19.98 mmol) was added to methyl glycerate (2 g, 16.65 mmol) and heated the mixture at 80° C. under nitrogen for 2.5 h. The excess dimethylethyldiamine was removed on a rotary evaporator which gave N,N-dimethylethyl glyceramide in quantitative yield. The compound showed the following characteristics: IR (neat) 3924.93, 2947.15, 2863.66, 1652.72, 1538.16, 1461.38 $cm^{-1}$, $^{1}$H NMR (200 MHz, $CDCl_3$), δ 2.23 (s, 6H, $CH_3$), 2.37 (t, 2H, $CH_2$), 3.41 (t, 2H, $CH_2$), 3.80 (d, (t, 1 H, CH), 5.36 (br, 2H, OH), 7.60 (t, 1 H, NH), $^{13}$C NMR (50 MHz, $CH_3OD$), δ 36.58, 44.59, 44.71, 58.22, 64.36, 73.38, 174.16, MS (CI, isobutane), $MH^+$, 191.

To a solution of N,N-dimethylethyl glyceramide (1.1 g, 6.24 mmol) in dry methylene chloride (100 mL) was added palmitic acid (3.60 g, 14.04 mmol) followed by dicyclo hexylcarbodiimide (3.99 g, 19.34 mmol) and a catalytic amount of N,N-dimethylaminopyridine at 0° C. The reaction mixture was stirred at 0° C. under nitrogen for 3 h and then at room temperature overnight. Ethyl acetate was added and the solid precipitate was removed by filtration. The filtrate was concentrated on a rotary evaporator and the residue was purified on a silica gel column eluting first with hexane:ethyl acetate (7:3) to remove the less polar impurities and then with chloroform:methanol (9:1). Removal of the solvent gave 2,3-dipalmitoyl-N,N-dimethylethyl glyceramide (3.66 g, 5.61 mmol, 90% yield). The compound showed the following characteristics: $^{1}$H NMR (200 MHz, $CDCl_3$) δ 0.88 (t, $CH_3$), 1.26 (br, $CH_2$), 1.62 (m, $CH_2$), 1.82 (m, $CH_2$), 2.35 (m, $CH_2$,CH), 3.51 (s, $CH_3$), 4.52 (br, NH), $^{13}$C NMR (50 MHz, $CDCl_3$), δ 14.06, 22.64, 24.73, 24.81,29.07, 29.25, 29.31,29.45, 29.60, 29.64, 31.87, 33.90, 34.01,34.09, 36.46, 44.95, 57.42, 62.95, 71.63, 166.91,172.06, 173.14, MS (CI, isobutane), $M^+$, 653.

Methyl chloride (10 mL) was condensed by using dry ice/acetone condenser and added to the solution of 2,3-dipalmitoyl-N,N-dimethylethyl glyceramide (1 g, 0.015 moles) in dry tetrahydrofuran (20 mL) in a pressure reactor. The reactor containing the reaction mixture was heated at 70° C. in an oil bath for 2 h and then cool to room temperature. The excess methyl chloride was removed by passing nitrogen through the reactor and bubbled in the water. The solvent was removed on a rotary evaporator and the solid residue (1.02 g, 95%) was crystallized from methanol:ether. The compound trimethyl ammonium ethyl 2,3-dipalmitoyl glyceramide chloride showed the following characteristics: m.p. 78°–80° C., $^{1}$H NMR (200 MHz, $CDCl_3$), δ 0.88 (t, $CH_3$), 1.25 (br, $CH_2$), 1.58 (m, $CH_2$), 1.82 (m, $CH_2$), 2.32 (m, $CH_2$), 2.53 (m, CH), 3.41 (s, $CH_3$), 3.61 (br, NH), 430 NMR (50 MHz, $CDCl_3$), δ 14.02, 22.60, 24.73, 24.73, 24.68, 25.54, 29.05, 29.16, 29.27, 29.49, 29.62, 30.21,31.83, 33.93, 34.02, 34.07, 34.50, 48.95, 51.33, 54.19, 62.80, 65.25, 71.50, 168.38, 173.24, 174.26, MS (FAB), $C^+$, 668.

EXAMPLE 3

10 grams of trimethylammonium ethyl 2,3-dipalmitoyl glycerate chloride was heated to a temperature of 60° C. and dispersed into water of 60° C. under stirring to form a homogeneous fabric conditioning dispersion A.

EXAMPLE 4

10 grams of trimethylammonium ethyl 2,3 dipalmitoyl glyceramide chloride was used to prepare a homogeneous dispersion B as described in Example 3.

EXAMPLE 5

Two samples A and B were prepared by adding 1 gram of each of dispersion A and B (see Examples 3–4) to 1 liter of tap water of ambient temperature containing 0.001% by weight of sodium alkylbenzene sulfate to simulate the carry over of anionic detergent active from the wash. 800 ml of each of the two samples were put in a tergotometer pot and four pieces of terry towel (40 g total weight were added). The cloths were treated for 5 minutes at 60 rpm, spin dried and line dried. The dried fabrics were assessed for softness by an expert panel using a Round Robin test protocol. The softness scores ranged from "0—hard" to "2—very soft".

Two control samples were also prepared as described above. Control 1 contained a 5% dispersion of 1,2-ditallowyl oxy-3-trimethyl ammonio propane chloride and hardened tallow fatty acid in a ratio of 6:1. Control 2 contained 5% Arquat 2HT which is dihardened tallow dimethyl ammonium chloride.

The softening scores for the four samples were as follows:

TABLE 1

| Active | Softness Score |
|---|---|
| Control 1 | 0.00 |
| Control 2 | 1.45 |
| Sample A | 0.31 |
| Sample B | 1.26 |

It was observed that sample B gave significantly better softening performance than the biodegradable compound of the Control 1 and a parity softening performance with the conventional softening compound of Control 2. Sample A gave a softening performance better than that of the biodegradable compound of Control 1.

EXAMPLE 6

The biodegradability of the compounds of examples 1 and 2 were evaluated by a Modified Sturm test and the results are indicated in the Table below:

| | % Biodegradation Day | | |
|---|---|---|---|
| Sample | 9 | 20 | 29 |
| 20 mg/l Las reference | 35 | 66 | 70 |
| 10 mg/l GAQ | 10 | 37 | 63 |
| 20 mg/l GAQ | 28 | 54 | 69 |
| 10 mg/l GEQ | 50 | 74 | 85 |
| 20 mg/l GEQ | 53 | 69 | 74 |

Although the ester linked compound degraded faster than the NH linked compound, both compounds exhibited a useful biodegradation of at least about 70% in 29 days.

The Modified Sturm test procedure

The Modified Sturm Test was adopted by the OECD on May 12, 1981 and renamed as the 301 B $CO_2$ Evolution Test in early 1993, herein incorporated by reference.

A high biodegradation result in this test provides the evidence that the test compound is highly biodegradable in aerobic systems.

The test is started by bubbling $CO_2$-free air through the solution at a rate of 50–100 ml/min per carboy (approximately 1–2 bubbles/second). The $CO_2$ produced in each carboy reacts with the barium hydroxide and is precipitated out as barium carbonate; the amount of $CO_2$ produced is determined by titrating the remaining $Ba(OH)_2$ with 0.05 N standardized HCl (see below). Periodically (every 2 or 3 days), the $CO_2$ absorber nearest the carboy is removed for titration. The remaining two absorbers are each moved one place closer to the carboy, and a new absorber filled with 100 ml of fresh 0.025 N $Ba(OH)_2$ is placed at the far end of the series. Titrations are made as needed (before any $BaCO_3$ precipitate is evident in the second trap), approximately every other day for the first 10 days, and the every fifth day until the 28th day.

For water-insoluble test materials, incorporated dry into the $CO_2$ test carboy, agitation can be done with a magnetic stirrer. For foaming chemicals, $CO_2$ test carboy, agitation can be done with a magnetic stirrer. For foaming chemicals, $CO_2$-free air bubbling can be replaced by overhead aeration and magnetic stirring.

On the 26th day, the pH of the carboy contents is measured again, and then 1 ml of concentrated HCl is added to each of the test carboys to drive off inorganic carbonate. The carboys are aerated overnight, and samples are removed from each carboy for dissolved organic carbon (DOC) analysis. The final titration is made on day 28.

Titrations of the 100 ml $Ba(OH)_2$ solution are made after removing the bottles closest to the carboys. The $Ba(OH)_2$ is titrated with 0.05 N HCl, using phenophthalein as an indicator.

The test is run at room temperature and temperature is recorded during the test period.

Theoretical amount of $CO_2$ is compared to amount of $CO_2$ produced to determine the biodegradation of a test material.

We claim:

1. A compound having a formula

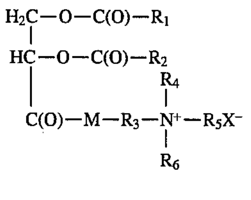

wherein $R_1$ and $R_2$ are each independently a $C_{15}$ to $C_{28}$ branched or straight chain alkyl, alkenyl or hydroxyalkyl, $R_3$ is a $C_{2-6}$ straight or branched alkyl, alkenyl or aryl, $R_4$, $R_5$ and $R_6$ are each independently a $C_{1-6}$ straight or branched alkyl, alkenyl, aryl or H provided that at least two of $R_4$, $R_5$ and $R_6$ are not H, M is O, NH or $NR_7$, $R_7$ is a $C_{1-6}$ unsubstituted or hydroxy substituted alkyl or alkenyl and $X^-$ is an anion which is watersoluble.

2. The compound according to claim 1 wherein $R_1$ and $R_2$ are each independently a $C_{15}$ to $C_{28}$ branched or straight chain alkyl, $R_3$ is a $C_{1-6}$ straight chain alkyl, $R_4$, $R_5$ and $R_6$ are each independently a $C_{1-6}$ straight chain alkyl, and M is O or NH.

3. The compound according to claim 1 wherein $X^-$ is selected from the group consisting of a halide, a sulfate and a nitrate.

4. The compound according to claim 3 wherein $X^-$ is selected from the group consisting of chloride, bromide, iodide and sulfate.

5. A compound according to claim 4, wherein $X^-$ is methyl sulfate.

6. The compound according to claim 1 wherein the compound is trimethylammonium ethyl 2,3-dipalmitoyl glyceramide chloride.

7. The compound according to claim 1 wherein the compound is trimethylammonium ethyl 2,3-dipalmitoyl glycerate chloride.

8. A composition for conditioning fabrics comprising:

a) 1 to 99% wt. % of a compound having a formula

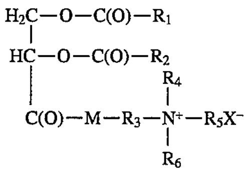

wherein $R_1$ and $R_2$ are each independently a $C_{15}$ to $C_{28}$ branched or straight chain alkyl, alkenyl or hydroxyalkyl, $R_3$ is a $C_{1-6}$ straight or branched alkyl, alkenyl or aryl, $R_4$, $R_5$ and $R_6$ are each independently a $C_{1-6}$ straight or branched alkyl, alkenyl, aryl or H provided that at least two of $R_4$, $R_5$ and $R_6$ are not H, M is 0, NH or $NR_7$, $R_7$ is a $C_{1-6}$ unsubstituted or hydroxy substituted alkyl or alkenyl and $X^-$ is an anion which is watersoluble; and b) 99% to 1% wt. water to form a dispersion.

9. The composition according to claim 8 wherein $R_1$ and $R_2$ are each independently a $C_{15}$ to $C_{28}$ branched or straight chain alkyl, $R_3$ is a $C_{1-6}$ straight chain alkyl, $R_4$, $R_5$ and $R_6$ are each independently a $C_{1-6}$ straight chain alkyl and M is O or NH.

10. The composition according to claim 8 wherein $X^-$ is selected from the group of a halide, a sulfate and a nitrate.

11. The composition according to claim 10 wherein $X^-$ is selected from the group consisting of chloride, bromide, iodide and sulfate.

12. The composition according to claim 11 wherein $X^-$ is methyl sulfate.

13. The composition according to claim 8 wherein the compound is trimethylammonium ethyl 2,3-dipalmitoyl glyceramide chloride.

14. The composition according to claim 8 wherein the compound is trimethylammonium ethyl 2,3-dipalmitoyl glycerate chloride.

* * * * *